United States Patent [19]

Schepens et al.

[11] Patent Number: 5,400,092
[45] Date of Patent: Mar. 21, 1995

[54] BINOCULAR OPHTHALMOSCOPE

[75] Inventors: Charles L. Schepens, Nahant; Yakov M. Reznichenko, Newton, both of Mass.

[73] Assignee: Mira, Inc., Waltham, Mass.

[21] Appl. No.: 808,752

[22] Filed: Dec. 17, 1991

[51] Int. Cl.[6] ............................................. A61B 3/10
[52] U.S. Cl. .................................. 351/214; 351/205; 351/220
[58] Field of Search .................... 351/205, 214, 220

[56] References Cited

U.S. PATENT DOCUMENTS

| | | | |
|---|---|---|---|
| 3,475,082 | 4/1967 | Strietzel | 351/205 |
| 3,582,191 | 6/1971 | Cohen . | |
| 4,015,898 | 4/1977 | Schirmer . | |
| 4,449,797 | 5/1984 | Kocher et al. . | |
| 4,669,839 | 6/1987 | Muchel . | |
| 4,671,631 | 6/1987 | Sigelman . | |
| 4,682,866 | 7/1987 | Volk | 351/205 |
| 4,684,227 | 8/1987 | Schmidt et al. | 351/205 |
| 4,710,000 | 12/1987 | Spitznas et al. | 351/205 |
| 4,710,002 | 12/1987 | Pomerantzeff . | |
| 4,738,521 | 4/1988 | Volk | 351/205 |
| 4,838,678 | 6/1989 | Hubertus . | |
| 4,900,143 | 2/1990 | Bessler et al. . | |
| 4,978,212 | 12/1990 | Hazard . | |

OTHER PUBLICATIONS

Hovland, K. R. and Schepens, C. L., "Clinical Evaluation of the Small-Pupil Binocular Indirect Ophthalmoscope", *Arch. Ophthal*, vol. 82, Oct. 1969.
Maxiscope Product Information No date.
Schepens Pomerantzeff Ophthalmoscope Operating and Maintenace Instructions Mar. 1990.

*Primary Examiner*—William L. Sikes
*Assistant Examiner*—Hung Xuan Dang
*Attorney, Agent, or Firm*—Hamilton, Brook, Smith & Reynolds

[57] ABSTRACT

A magnifying binocular ophthalmoscope that employs a telecentric ocular lens in front of a viewing mirror assembly in order to provide parallel light rays from the lens to the viewing mirror assembly and from there to two direction changing mirrors that direct the light to the viewer's eyes. Also disclosed is the use of prisms between an objective lens and an ocular lens, the prisms redirecting the optical paths from the viewing mirror assembly and causing the optical path to cross its path within the prism so as to increase the length of the path and invert the image vertically and horizontally. Also disclosed is an assembly for illuminating and directing light that includes first and second stages that are movable along a viewing direction and carry respective first and second mirrors, the second stage being mounted for both movement with the first stage and movement relative to the first stage.

9 Claims, 5 Drawing Sheets

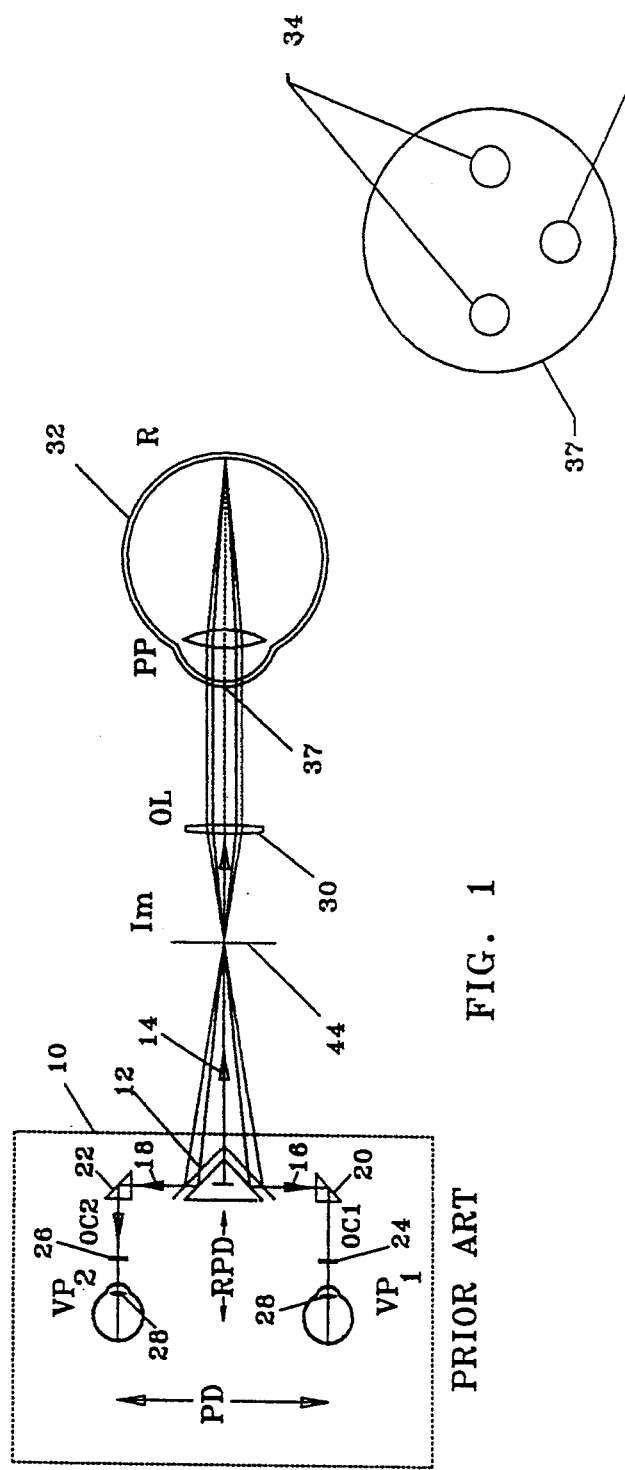
FIG. 1 PRIOR ART
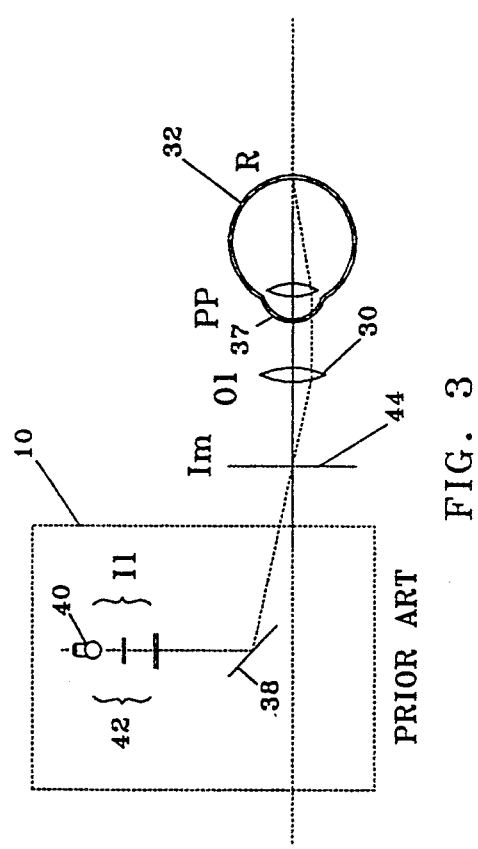
FIG. 2
FIG. 3 PRIOR ART

BINOCULAR OPHTHALMOSCOPE

The invention relates to magnifying binocular ophthalmoscopes and illuminating systems useful therein.

BACKGROUND OF THE INVENTION

Binocular indirect ophthalmoscopes are used by an ophthalmologist to look into a patient's eye. A unit is strapped onto the ophthalmologist's head, and he holds an ophthalmoscopic lens at arm's length close to the patient's eye, as is discussed in Hovland, K. R. and Schepens, C. L., "Clinical Evaluation of the Small-Pupil Binocular Indirect Ophthalmoscope", Arch Ophthal, Vol. 82, October 1969. The unit on the ophthalmologist's head has movable mirrors in order to place images of the observer's two pupils and a light source in the patient's pupil. The head unit accommodates observers having different distances (PD) between their pupils and also has adjustment of the reducing pupil distance (RPD) mechanism in order to adjust the distance between the images of the viewer's two pupils within the patient's pupil. There also typically is movement of a mirror directing light from the illumination source to adjust the distance of the illumination source image from the viewing pupils images within the patient's pupil.

FIGS. 1–3 describe a prior art binocular ophthalmoscope system. Ophthalmologist head unit 10 includes viewing mirror assembly 12 having two reflective surfaces at approximately 45° to the viewing direction along axis 14. These surfaces provide two optical paths 16, 18 perpendicular to the viewing direction. Mirrors 20, 22 are spaced from each other by the distance PD and redirect the optical paths 90°. The redirected optical paths extend through ocular lenses 24, 26 to the observer's pupils 28. Ophthalmoscopic lens 30 is held close to the patient's eye 32 and provides an image at image plane 44. The distance from the viewing pupils 28 to lens 30 is known as the working distance (WD). Viewing mirror assembly 12 is moved forward or backward along the viewing direction of axis 14 (as indicated by the RPD arrows in FIG. 1) in order to change the distance between the images of the observer's pupils 34, shown with the image of the illumination source 35, in the patient's pupil 37 in FIG. 2. When assembly 12 is moved forward, as indicated by dashed lines in FIG. 1, the images of the viewer's pupils 34 will be further apart in the patient's pupil 37. Owing to the diverging nature of the light rays from image plane 44, in some head units 10, e.g., the S-P Ophthalmoscope sold by MIRA, Inc., Waltham, Mass., the reflective surfaces of mirror assembly 12 are adjusted angularly with forward and backward movements of assembly 12. In some other head units, e.g., the one shown U.S. Pat. No. 4,684,227, there is no such angular adjustment, with a possible resulting effect on the quality of the stereo image.

Referring to FIG. 3, showing the illumination system of a prior art binocular ophthalmoscope, mirror 38, which is separate from mirror assembly 12, is used to direct light from light source 40 and lens system 42 to the patient's eye 32. Ophthalmoscopic lens 30 provides an image of light source 40 to the patient's pupil 37. In some prior art binocular ophthalmoscopes, the illumination mirror is moved independently of the viewing mirror assembly, which typically is located underneath it. In some other prior art binocular ophthalmoscopes, the illumination mirror is fixedly mounted with respect to the viewing mirror assembly and thus moves with it.

Hubertus U.S. Pat. No. 4,838,678 describes a binocular ophthalmoscope employing plano-convex lens 19 as part of the objective lens system with lenses 28. The ophthalmoscope also includes eye-piece 34 (including an ocular lens) and Schmidt or Pechan prism 42 to fold the rays of light within it and re-invert the image.

SUMMARY OF THE INVENTION

In one aspect, the invention features, in general, a binocular ophthalmoscope that employs a telecentric ocular lens in front of a viewing mirror assembly in order to provide parallel light rays from the lens to the viewing mirror assembly and from there to two direction changing mirrors that direct the light to the viewer's eyes. By providing parallel rays of light to the viewing mirror assembly, the need for angular adjustment of the mirror assembly with the forward and backward movement is avoided without loss of image quality. This arrangement also provides for advantages in magnification, in that, by having the ocular lens in front, one can decrease the focal length (and increase magnification) without decreasing the working distance. Also, one can get a higher magnification with a wider field by using higher power (short focal length) ophthalmoscopic lenses.

In preferred embodiments, the telecentric ocular lens is removably mounted so as to permit the use of interchangeable lenses having different powers, thus providing different magnification while still maintaining the parallel nature of the light rays. The ophthalmoscope also employs an illumination system that directs light along an optical path through the telecentric ocular lens, providing uniform brightness for different magnifications.

In another aspect, the invention features, in general, a binocular ophthalmoscope employing a pair of objective lenses mounted on opposite sides of the viewing mirror assembly along respective optical paths from the assembly, a pair of prisms mounted outside of the objective lenses, and a pair of ocular lenses between the prisms and the viewer's eyes. The prisms have reflective surfaces that are positioned to redirect the optical paths so as to exit the prisms along the paths that are generally parallel to the viewing direction. The reflective surfaces also cause the optical path to cross its path within the prism so as to increase the length of the path. The reflective surfaces also cause the image to invert vertically and horizontally. This arrangement provides the magnification advantages associated with having an objective lens and an ocular lens and employs the prisms both to change the direction of the optical path at the width of the viewer's eyes and to provide for the necessary inversion of the image created by the use of an additional lens.

In preferred embodiments the prisms are pentaprisms that each have a "roof configuration", i.e., a pair of reflective surfaces at a 90 degree angle with each other in the vertical direction so as to provide a vertical inversion of the image.

In another aspect, the invention features, in general, an assembly for illuminating and directing light from an object. The assembly includes first and second stages that are movable along a viewing direction and carry respective first and second mirrors. (e.g., the first mirror could be in the viewing mirror assembly of a binocular ophthalmoscope and the second mirror could be in the illumination system.) The second stage is mounted for both movement with the first stage and movement relative to the first stage. This permits the first and second mirrors to desirably be moved as a unit along the direction of sight and also permits for the fine tuning adjustments of the relative positions of the two mirrors by movement of the second mirror relative to the first.

In preferred embodiments there are independent mechanisms to move the two stages, and the second stage is slidably mounted on the first stage such that substantial friction must be overcome to cause relative sliding between the two.

Other advantages and feature is of the invention will be apparent from the following description of the preferred embodiments thereof and from the claims.

DESCRIPTION OF THE PREFERRED EMBODIMENTS

The drawings will be described first.

DRAWINGS

FIG. 1 is a diagram of a prior art binocular ophthalmoscope.

FIG. 2 is diagram showing the positions of images of the observer's pupils and the illumination source in the patient's pupil.

FIG. 3 is a diagram of a prior art illuminating system for a binocular ophthalmoscope.

STRUCTURE AND OPERATION

Figure 4:
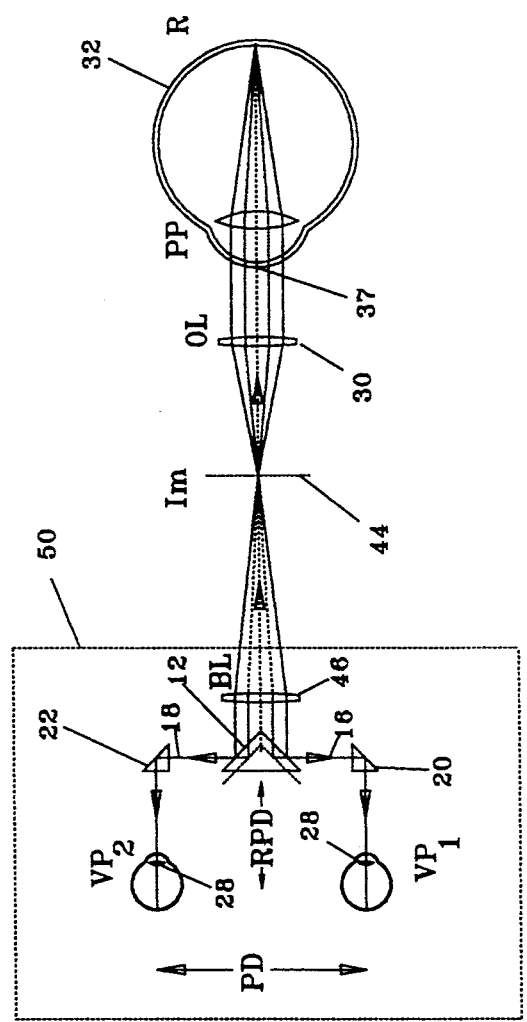
FIG. 4 is diagram of components of a binocular ophthalmoscope according to the invention.

Referring to FIG. 4, a binocular ophthalmoscope according to the invention is shown. The components of the FIG. 4 ophthalmoscope that are in common with those of the prior art ophthalmoscope shown in FIG. 1 have common references numbers. Unit 50, which is strapped to the ophthalmologist's head, employs viewing mirror assembly 12 and mirrors 20, 22 to direct optical paths to the observer's eyes 28. Viewing mirror assembly 12 is movable forward and backward to adjust the RPD by a mechanism not shown. Mirrors 20, 22 are likewise movable to adjust the distance PD to accommodate different distances between observer's eyes by a mechanism not shown. These mechanisms are well known in the art. Unit 50 employs a telecentric ocular lens 46, which provides parallel light rays from it to viewing mirror assembly 12 and along optical paths 16, 18 to viewer's eyes 28.

Figure 5:
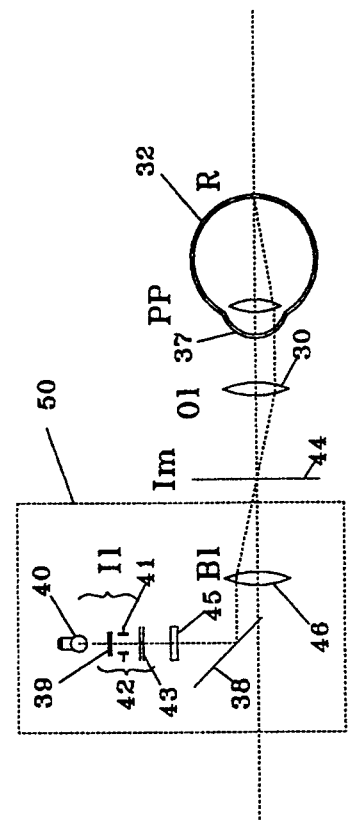
FIG. 5 is a diagram of the illuminating system of the FIG. 4 ophthalmoscope.

Referring to FIG. 5, light from light source 40 is collimated by condensing lens 39, passes through diaphragm 41 (located in the focal plane of objective lens 43), and is focused in optical filter plane 45 (which is ideally located at the same distance from mirror 38 as pupils 28 are from viewing mirror assembly 12). From plane 45, the light is reflected by mirror 38 and passes through telecentric ocular lens 46, forming an image of diaphragm 39 in image plane 44. After passing through ophthalmoscopic lens 30, light is focused in the patient pupil plane. By changing ocular lens 46 it is possible to change the illumination diameter in image plane 44 without changing the intensity of light. Such an optical configuration provides uniform image illumination for different magnifications, and reduces the illumination pupil diameter in the patient pupil plane.

Figure 6:
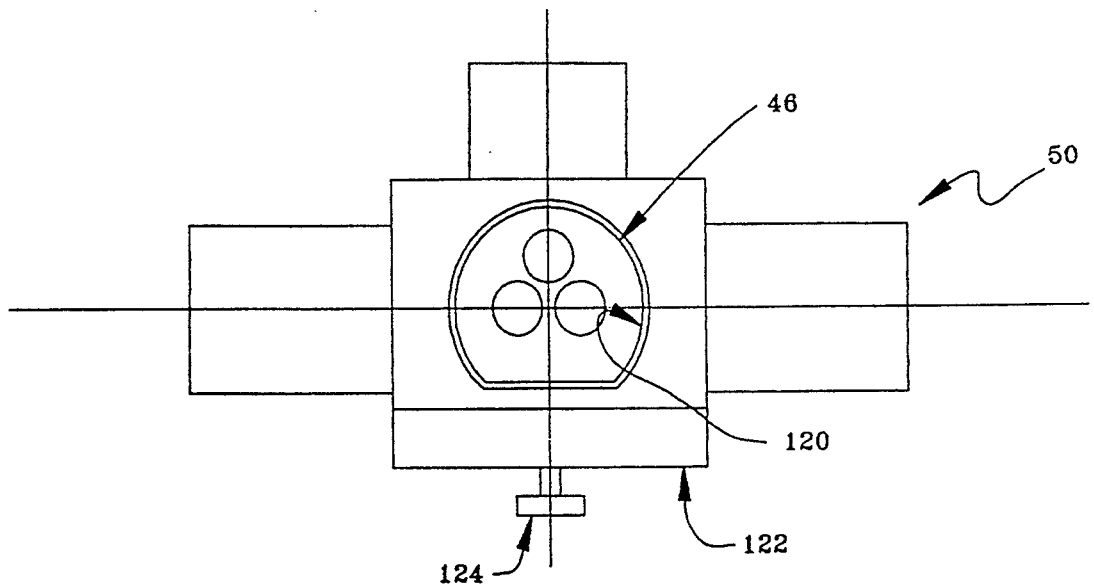
FIG. 6 is an elevation of a unit of the FIG. 4 ophthalmoscope.

Referring to FIG. 6, lens 46 is removably retained in recess 120 of housing 122 of unit 50 by locking screw 124, which engages the bottom surface of lens 46. Three different lenses 46 can be employed. One has power of 6.7 D and a 150 mm focal length. Another has a power of 4 D and a focal length of 250 mm. The third has a power of 10 D and a 100 mm focal length. Also, five different ophthalmoscopic lenses 30 can be used, having powers of 14 D, 20 D, 30 D, 40 D, and 60 D, in the combinations shown in the table below, to provide the indicated magnifications, fields of view in air, patient pupil diameters, and observation distances (OD). The observation distance is the distance between the binocular lens and the aerial image. In the table below ophthalmoscopic lenses 30 are indicated OL.

| Optical Parameters Variations Depending on Combinations of Oculars, Back Focal Lengths and Ophthalmoscopic Lenses | | | |
|---|---|---|---|
| Observation Distance | Magnification | Field of View | Pupil Diameter |
| 1. OD = 150 mm | | | |
| OL = 14 D (f = 71 mm) | 7* | 20° | 8 mm |
| OL = 20 D (f = 50 mm) | 5* | 30° | 6 mm |
| OL = 30 D (f = 33 mm) | 3.5* | 45° | 4 mm |
| OL = 40 D (f = 25 mm) | 2.5* | 60° | 3 mm |
| OL = 60 D (f = 17 mm) | 1.7* | 80° | 2 mm |
| 2. OD = 250 mm | | | |
| OL = 14 D (f = 71 mm) | 5* | 25° | 6 mm |
| OL = 20 D (f = 50 mm) | 3* | 30° | 4 mm |
| OL = 30 D (f = 33 mm) | 2* | 45° | 2.5 mm |
| OL = 40 D (f = 25 mm) | 1.5* | 60° | 2 mm |
| OL = 60 D (f = 17 mm) | | | |
| 3. OD = 400 mm | | | |
| OL = 14 D (f = 71 mm) | 3* | 30° | 4 mm |
| OL = 20 D (f = 50 mm) | 2* | 40° | 2.5 mm |
| OL = 30 D (f = 33 mm) | 1.5* | 45° | 2 mm |
| OL = 40 D (f = 25 mm) | | | |

In use of the system shown in FIGS. 4–6, unit 50 is strapped on to the ophthalmologist's head, and lens 30 is held in front of the patient's pupil. Mirrors 20, 22 are moved to accommodate the distance between pupils (PD) for the particular observer, who also adjusts the reducing pupil distance (RPD) mechanism in order to adjust the distance between the images of the viewer's two pupils within the patient's pupil. Mirror 38 (FIG. 5) is also adjusted forward or backward to adjust the distance of the illumination source image from the 'viewing pupils' images within the patient's pupil. Telecentric ocular lens 46 provides parallel rays of light to the viewing mirror assembly 12 and along paths 16, 18 to the viewing pupils; there is no need for angular adjustment of the mirrors of assembly 12 with the forward and backward movement and no loss of image quality. This arrangement also provides for advantages in magnification, in that by having ocular lens 46 in front, one can decrease the focal length (and increase magnification) without decreasing the working distance. Also, one gets a higher magnification with a wider field by using, for the same magnification, higher power and wider field ophthalmoscopic lenses. Because the light from the illumination source goes through lens 46, changing lens 46 to change the magnification changes the illumination diameter 35, and, as a result, brightens the images uniformly for the range of magnification and field of view.

Figure 7:
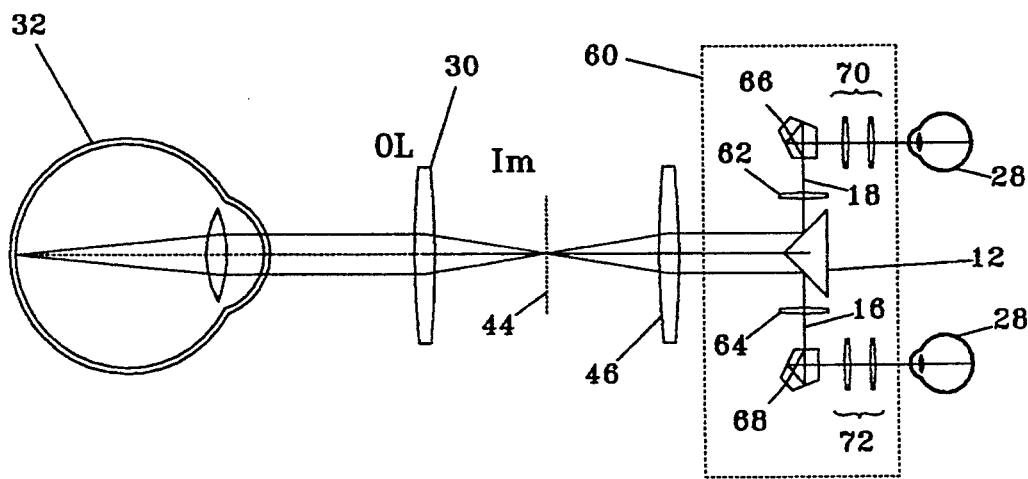
FIG. 7 is a diagram of a different embodiment of a binocular ophthalmoscope according to the invention.

Referring to FIG. 7, there is shown a binocular ophthalmoscope system including a unit 60 that is strapped onto the ophthalmologist's head. It includes a binocular lens 46 that is removably mounted, and a movable viewing mirror assembly 12, to provide two optical paths 16, 18. Objective lenses 62, 64 are mounted along respective paths 16, 18, as are pentaprisms 66, 68. The paths exiting pentaprisms 66, 68 are redirected at 90° and passed through ocular lenses 70, 72 to the viewer's eyes 28. Each prism 66, 68 has reflective surfaces that are positioned to cause the optical path to cross its path within the prism so as to increase the length of the path, thus accommodating longer focal lengths for the lenses without increasing the size of the head unit. The reflective surfaces also cause the image to invert vertically and horizontally.

Figure 8:
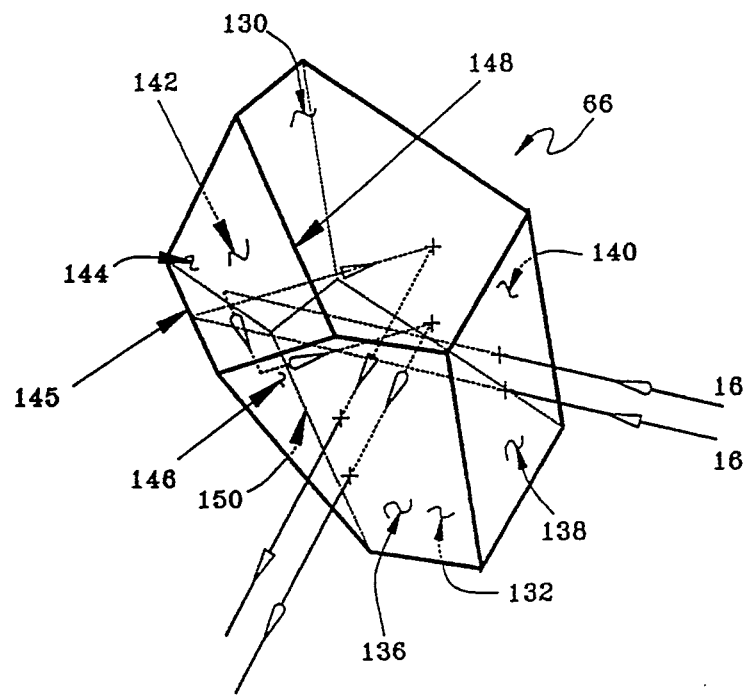
FIG. 8 is a perspective view of a pentaprism component of the FIG. 7 ophthalmoscope.

Referring to FIG. 8, prism 66 (prism 68 is identical) has parallel top and bottom surfaces 130, 132; four vertical surfaces 136, 138, 140, 142; and two surfaces 144, 146 that are at a 90 degree angle with each other and 45 degree angles with the horizontal. Light enters through surface 138, is reflected by surfaces 144, 146, and 140, and exits through surface 136. The plane through edge 148 (between surface 130 and 144) and edge 150 (between surface 146 and surface 132) makes a 112.5 degree angle with surface 136. The plane just defined makes a 45 degree angle with surface 140. Surface 138 makes a 112.5 degree angle with surface 140. The 112.5 degree and 45 degree angles are common for such pentaprisms, though the surface 144 and 146 at a 90 degree angle with each other and at 45 degree angles with the horizontal are not common. Optical path 16 enters at the center of surface 138 and it is redirected at the junction of surfaces 144, 146 to surface 140 and surface 136. Optical path 16' is higher than path 16 at the entrance, but is lower at the exit, as it is redirected from surface 144 vertically downward to surface 146 before being redirected to surface 140. Similarly, a path under center path 16 at surface 138 exits above it at surface 136. A path to the right of path 16 at surface 138 is on the left side coming out at surface 136. The image coming out is thus inverted both vertically and horizontally from that going in, unlike a typical pentaprism (which has a planar reflective surface at the plane through edges 148, 150 instead of surfaces 144, 146), which inverts the image horizontally but not vertically.

The arrangement of FIG. 7 provides the higher magnification advantages associated with having an objective lens and an ocular lens and employs prisms 66, 68 to perform the dual functions of changing the direction of the optical path at the width of the viewer's eyes and providing for the necessary inversion of the image created by the use of an additional lens. In addition, prisms 66, 68 achieve these goals with only three reflections, thus limiting the losses associated with reflections. A further advantage of prisms 66, 68 is that they are insensitive to slight angular variation with respect to the optical paths 16, 18, so that some variation of or lack of precision in orientation of prisms 66, 68 during mounting will not detrimentally affect operation.

As with the FIGS. 4 and 5 embodiment, the FIGS. 7 and 8 embodiment can be used with the same three different lens 46 and with the same five different ophthalmoscopic lenses 30 in the combinations shown in the table below, to provide the indicated magnifications, fields of view in air, patient pupil diameters, and observation distances (OD).

| Optical Parameters Variations Depending on Combinations of Oculars, Back Focal Lengths and Opthalmoscopic Lenses | | | |
|---|---|---|---|
| Observation Distance | Magnification | Field of View | Pupil Diameter |
| 1. OD = 150 mm | | | |
| OL = 14 D (f = 71 mm) | 20* | 20° | 10 mm |
| OL = 20 D (f = 50 mm) | 15* | 30° | 7 mm |
| OL = 30 D (f = 33 mm) | 10* | 45° | 4 mm |
| OL = 40 D (f = 25 mm) | 7.5* | 60° | 3.5 mm |
| OL = 60 D (f = 17 mm) | 5* | 80° | 2.3 mm |
| 2. OD = 250 mm | | | |
| OL = 14 D (f = 71 mm) | 12* | 25° | 6 mm |
| OL = 20 D (f = 50 mm) | 9* | 30° | 4 mm |
| OL = 30 D (f = 33 mm) | 5* | 45° | 2.5 mm |
| OL = 40 D (f = 25 mm) | 4.5* | 60° | 2 mm |
| OL = 60 D (f = 17 mm) | 3* | 80° | 1.3 mm |
| 3. OD = 400 mm | | | |
| OL = 14 D (f = 71 mm) | 7.5* | 25° | 4 mm |
| OL = 20 D (f = 50 mm) | 5.6* | 35° | 2.5 mm |
| OL = 30 D (f = 33 mm) | 3.7* | 45° | 1.6 mm |
| OL = 40 D (f = 25 mm) | 2.8* | 60° | 1.25 mm |

Figure 9:
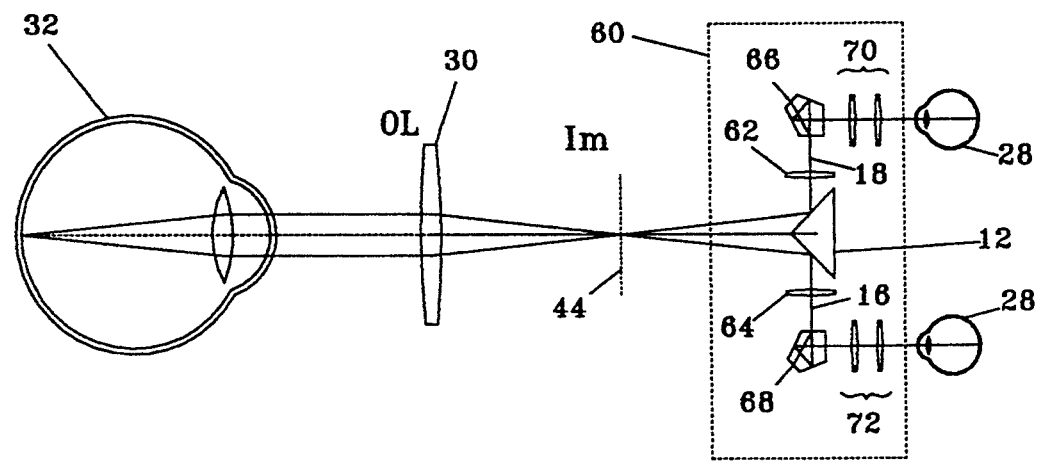
FIG. 9 is a diagram of yet another embodiment of a binocular ophthalmoscope according to the invention.

FIG. 9 describes a system that is similar to FIG. 7 except that it does not employ binocular lens 46. In this embodiment, changes in RPD would require changes in the working distance.

Figure 10:
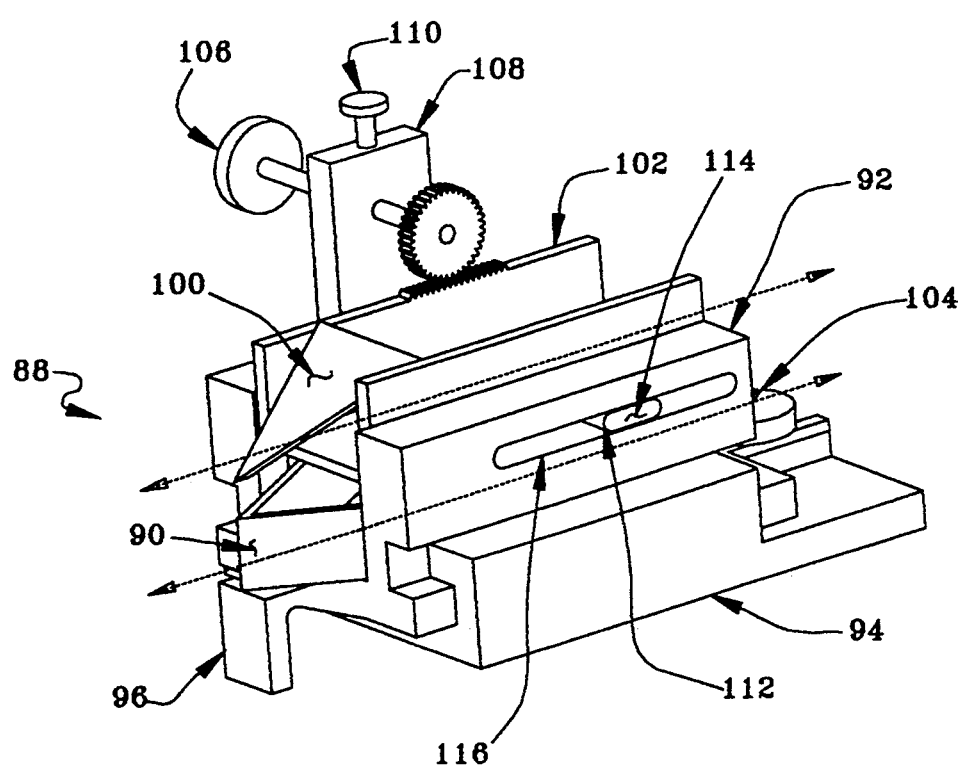
FIG. 10 is a perspective view of an adjustable mirror assembly which can be used in binocular ophthalmoscopes according to the invention.

Referring to FIG. 10, there is shown optical assembly 88 that can be used in the binocular ophthalmoscopes described herein or in other applications. Viewing mirror assembly 90 is mounted on first stage 92 for sliding movement along the viewing direction axis with respect to base 94 by manually pulling slide adjustment tab 96. Illumination mirror 100 is mounted on second stage 102 for sliding along a parallel axis, either with first stage 92 or relative to first stage 92. First stage 92 can be locked with respect to base 94 by tightening locking screw 104. Second stage 102 can be moved relative to base 94 by rotation of knob 106, mounted on support 108, attached to base 94. Locking screw 110 can be tightened to lock knob 106. Compression slide 112 is mounted on second stage 102 and has ends 114 in slots 116 of first stage 92. (Only one end 114 and one slot 116 are shown in FIG. 10.) Ends 114 have a thickness slightly greater than the height of slot 116, and provide a sufficiently high coefficient of friction so as to cause the two stages to move with each other unless one of the locking screws are tightened; in this case, slide 112 slides within slot 116. If locking screw 104 is tightened, and locking screw 110 is not, rotation of knob 106 causes only second stage 102 to move. If locking screw 110 is tightened, and locking screw 104 is not, pushing or pulling of tab 96 causes only first stage 92 to move. If both locking screws are not tightened, the two stages will move together when either tab 96 or knob 106 are activated. This permits viewing mirror assembly 90 and illumination mirror 100 to desirably be moved as a unit along the direction of sight and also permits for the fine tuning adjustments of the relative positions of the two sets of mirrors 90, 100 and the independent movement of the two sets of mirrors 90, 100.

Other embodiments of the invention are within the scope of the claims.

What is claimed is:

1. A head mounted binocular ophthalmoscope comprising:
   a support structure having a strap to mount the support structure on a viewer's head,
   a viewing mirror assembly centrally mounted for movement along a viewing direction on said support structure, said viewing mirror assembly having mirrors mounted to provide two optical paths generally perpendicular to said viewing direction and extending in opposite directions from said viewing mirror assembly,
   objective lenses mounted on said support structure on opposite sides of said viewing mirror assembly along the two respective optical paths,
   spaced prisms mounted on said support structure on opposite sides of said viewing mirror assembly along respective said optical paths outside of said objective lenses and spaced from each other by the distance between the viewer's eyes, said prisms having surfaces providing reflections to redirect said optical paths entering said prism so as to exit said prisms along paths that are generally parallel to said viewing direction and each other and spaced from each other by said distance equal to the spacing between the viewer's eyes, said reflective surfaces causing said optical path to cross its path within said prism so as to increase the length of the path, said reflective surfaces also causing the image to be inverted vertically and horizontally, and
   ocular lenses in respective said optical paths exiting said prisms.

2. The ophthalmoscope of claim 1 wherein said prism is a pentaprism with a pair of reflective surfaces at 90 degree angle with each other in a vertical cut so as to provide a vertical inversion of the image.

3. The ophthalmoscope of claim 2 further comprising a telecentric ocular lens in front of said mirror assembly providing parallel light rays from it to said viewing mirror assembly.

4. The ophthalmoscope of claim 3 wherein said telecentric ocular lens is removably mounted so as to permit use of interchangeable lenses having different power.

5. The ophthalmoscope of claim 4 further comprising an illumination system that directs light along an optical path through said telecentric ocular lens.

6. A binocular ophthalmoscope for directing illuminating light to an object being viewed and directing light from the illuminated object comprising;
   a first stage that is movable along a viewing direction,
   a first mirror assembly that is carried on said first stage and oriented to direct light from said illuminated object along a first path and a second path which are transverse to said viewing direction,
   a pair of mirrors or prisms mounted to reflect light along the first path and second path,
   a second stage that is movable along said viewing direction and is adjustably mounted relative to said first stage to selectively have movement with said first stage or movement relative to said first stage and the first mirror assembly, and
   a second mirror that is carried on said second stage and oriented to direct light from a source to said object, said light traveling from said source along a second path that is transverse to the viewing direction, the second mirror being movable with the first stage along the viewing direction, or alternatively, being movable relative to the first stage.

7. The assembly of claim 6 wherein said first mirror assembly receives light from the object through an ocular lens mounted on a support structure relative to the first mirror assembly.

8. The optical assembly of claim 6, further comprising spaced prisms for directing light from said viewing direction to an optical path 90° to said viewing direction, said spaced prisms being spaced from each other by the distance between the viewer's eyes, said spaced prisms having surfaces providing reflections to redirect said optical paths entering said prism so as to exit said spaced prisms along paths that are generally parallel to said viewing direction and each other and spaced from each other by said distance equal to the spacing between the viewer's eyes, said reflective surfaces causing said optical path to cross its path within said prism so as to increase the length of the path, said reflective surfaces also causing the image to be inverted vertically and horizontally.

9. A binocular ophthalmoscope comprising:
   a support structure;
   a viewing mirror assembly centrally mounted for movement along a viewing direction on said support structure, said viewing mirror assembly having mirror mounted to provide two optical paths generally perpendicular to said viewing direction and extending in opposite directions from said viewing mirror assembly;
   a pair of spaced prisms mounted on said support structure on opposite sides of said viewing mirror assembly along respective said optical paths and spaced from each other by the distance between the viewer's eyes, said spaced prisms being oriented to redirect said optical paths from said assembly so as to be generally parallel to said viewing direction and each other and spaced from each other by said distance equal to the spacing between the viewer's eyes;
   an ocular lens in front of said viewing mirror assembly providing parallel light rays from the ocular lens to said viewing mirror assembly and along said paths to the viewer's eyes whereby a telecentric lens is formed, the spaced prisms being mounted on said support structure on opposite sides of said assembly along respective said optical paths and spaced from each other by the distance between the viewer's eyes, said prisms each having surfaces providing a plurality of reflections to redirect said optical paths entering said prism so a to exit said prism along paths that are generally parallel to said viewing direction and each other and spaced from each other by said distance equal to the spacing between the viewer's eyes, said reflective surfaces causing said optical path to cross its paths within said prism so as to increase the length of the path, said reflective surfaces also causing the image to be inverted vertically and horizontally.

* * * * *